United States Patent
Subramanian et al.

(10) Patent No.: US 12,427,332 B2
(45) Date of Patent: Sep. 30, 2025

(54) PHOTOBIOMODULATION SYSTEM AND DELIVERY DEVICE AND METHODS OF MAKING AND USING

(71) Applicant: Boston Scientific Neuromodulation Corporation, Valencia, CA (US)

(72) Inventors: Hari Hara Subramanian, Valencia, CA (US); Joshua Dale Howard, Sacramento, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 547 days.

(21) Appl. No.: 17/714,748

(22) Filed: Apr. 6, 2022

(65) Prior Publication Data
US 2022/0323781 A1 Oct. 13, 2022

Related U.S. Application Data

(60) Provisional application No. 63/172,415, filed on Apr. 8, 2021.

(51) Int. Cl.
| | |
|---|---|
| *A61N 5/06* | (2006.01) |
| *A61B 1/00* | (2006.01) |
| *A61B 1/015* | (2006.01) |

(52) U.S. Cl.
CPC ........ *A61N 5/0603* (2013.01); *A61B 1/00087* (2013.01); *A61B 1/015* (2013.01);
(Continued)

(58) Field of Classification Search
CPC .......... A61N 2005/0632; A61N 5/0613; A61N 5/0601
(Continued)

(56) References Cited

U.S. PATENT DOCUMENTS

| 4,920,979 A | 5/1990 | Bullara |
|---|---|---|
| 5,076,270 A | 12/1991 | Stutz, Jr. |

(Continued)

FOREIGN PATENT DOCUMENTS

| EP | 2143373 A1 * | 1/2010 | ......... A61B 1/00117 |
|---|---|---|---|
| EP | 3020450 A1 | 5/2016 | |

(Continued)

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.
(Continued)

*Primary Examiner* — Michael J Carey
*Assistant Examiner* — Timothy Tuan Luu
(74) *Attorney, Agent, or Firm* — Branch Partners PLLC; Bruce E. Black

(57) ABSTRACT

A photobiomodulation system includes a) a control module having electronic subassembly disposed in a housing, a connector coupled to the housing and defining a connector lumen, and at least one light source to produce light in response to signals from the electronic subassembly; b) a lead coupled or coupleable to the control module and having a lead body defining a lead lumen and at least one opening along a distal portion of the lead, light emitters arranged along the distal portion of the lead, and optical fibers extending along the lead body and coupled to the light emitters; and c) a catheter assembly having a tube coupleable to a catheter pump, and a distal connector attached to the end of the tube and coupled or coupleable to the connector of the control module.

20 Claims, 7 Drawing Sheets

(52) U.S. Cl.
CPC .... *A61N 5/0613* (2013.01); *A61N 2005/0626* (2013.01); *A61N 2005/063* (2013.01)

(58) Field of Classification Search
USPC .................................. 604/20; 607/88, 92, 93
See application file for complete search history.

(56) References Cited

U.S. PATENT DOCUMENTS

| | | | |
|---|---|---|---|
| 5,437,193 A | 8/1995 | Schleitweiler et al. | |
| 5,445,608 A | 8/1995 | Chen et al. | |
| 5,556,421 A | 9/1996 | Prutchi et al. | |
| 5,824,027 A | 10/1998 | Hoffer et al. | |
| 6,175,710 B1 | 1/2001 | Kamaji et al. | |
| 6,181,969 B1 | 1/2001 | Gord | |
| 6,224,450 B1 | 5/2001 | Norton | |
| 6,271,094 B1 | 8/2001 | Boyd et al. | |
| 6,295,944 B1 | 10/2001 | Lovett | |
| 6,364,278 B1 | 4/2002 | Lin et al. | |
| 6,366,719 B1 | 4/2002 | Heath et al. | |
| 6,391,985 B1 | 5/2002 | Goode et al. | |
| 6,442,435 B2 | 8/2002 | King et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,895,280 B2 | 5/2005 | Meadows et al. | |
| 6,988,001 B2 | 1/2006 | Greatbatch et al. | |
| 6,993,384 B2 | 1/2006 | Bradley et al. | |
| 7,190,993 B2 | 3/2007 | Sharma et al. | |
| 7,203,548 B2 | 4/2007 | Whitehurst et al. | |
| 7,244,150 B1 | 7/2007 | Brase et al. | |
| 7,252,677 B2 | 8/2007 | Burwell et al. | |
| 7,288,108 B2 | 10/2007 | DiMauro et al. | |
| 7,395,118 B2 | 7/2008 | Erickson | |
| 7,437,193 B2 | 10/2008 | Parramon et al. | |
| 7,450,997 B1 | 11/2008 | Pianca et al. | |
| 7,596,414 B2 | 9/2009 | Whitehurst et al. | |
| 7,610,103 B2 | 10/2009 | Whitehurst et al. | |
| 7,672,734 B2 | 3/2010 | Anderson et al. | |
| 7,684,869 B2 | 3/2010 | Bradley et al. | |
| 7,736,382 B2 | 6/2010 | Webb et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,803,021 B1 | 9/2010 | Brase | |
| 7,809,435 B1 | 10/2010 | Ettare et al. | |
| 7,809,446 B2 | 10/2010 | Meadows | |
| 7,946,980 B2 | 5/2011 | Reddy et al. | |
| 7,949,395 B2 | 5/2011 | Kuzma | |
| 7,949,409 B2 | 5/2011 | Bly et al. | |
| 7,974,706 B2 | 7/2011 | Moffitt et al. | |
| 8,086,322 B2 | 12/2011 | Schouenborg | |
| 8,175,710 B2 | 5/2012 | He | |
| 8,224,450 B2 | 7/2012 | Brase | |
| 8,271,094 B1 | 9/2012 | Moffitt et al. | |
| 8,295,944 B2 | 10/2012 | Howard et al. | |
| 8,311,647 B2 | 11/2012 | Bly | |
| 8,326,433 B2 | 12/2012 | Blum et al. | |
| 8,340,785 B2 | 12/2012 | Bonde et al. | |
| 8,364,278 B2 | 1/2013 | Pianca et al. | |
| 8,386,054 B2 | 2/2013 | North | |
| 8,391,985 B2 | 3/2013 | McDonald | |
| 8,463,343 B2 | 6/2013 | Kuhn et al. | |
| 8,473,061 B2 | 6/2013 | Moffitt et al. | |
| 8,483,237 B2 | 7/2013 | Zimmermann et al. | |
| 8,525,027 B2 | 9/2013 | Lindner et al. | |
| 8,571,665 B2 | 10/2013 | Moffitt et al. | |
| 8,600,509 B2 | 12/2013 | McDonald et al. | |
| 8,675,945 B2 | 3/2014 | Barnhorst et al. | |
| 8,682,439 B2 | 3/2014 | DeRohan et al. | |
| 8,688,235 B1 | 4/2014 | Pianca et al. | |
| 8,792,993 B2 | 7/2014 | Pianca et al. | |
| 8,831,731 B2 | 9/2014 | Blum et al. | |
| 8,831,742 B2 | 9/2014 | Pianca et al. | |
| 8,831,746 B2 | 9/2014 | Swanson | |
| 8,849,632 B2 | 9/2014 | Sparks et al. | |
| 8,855,768 B1 | 10/2014 | Johnson et al. | |
| 8,868,211 B2 | 10/2014 | Durand et al. | |
| 8,897,876 B2 | 11/2014 | Sundaramurthy et al. | |
| 8,929,973 B1 | 1/2015 | Webb et al. | |
| 8,936,630 B2 | 1/2015 | Denison et al. | |
| 8,958,615 B2 | 2/2015 | Blum et al. | |
| 9,238,132 B2 | 1/2016 | Barker | |
| 9,409,032 B2 | 8/2016 | Brase et al. | |
| 9,415,154 B2* | 8/2016 | Leven | A61N 1/05 |
| 9,421,362 B2 | 8/2016 | Seeley | |
| 9,440,066 B2 | 9/2016 | Black | |
| 9,550,063 B2 | 1/2017 | Wolf, II | |
| 9,604,068 B2 | 3/2017 | Malinowski | |
| 9,643,010 B2 | 5/2017 | Ranu | |
| 9,656,093 B2 | 5/2017 | Villarta et al. | |
| 9,681,809 B2 | 6/2017 | Sharma et al. | |
| 9,770,598 B2 | 9/2017 | Malinowski et al. | |
| 9,931,511 B2 | 4/2018 | Kaula et al. | |
| 10,213,596 B2 | 2/2019 | Orinski | |
| 10,307,602 B2 | 6/2019 | Leven | |
| 10,335,607 B2 | 7/2019 | Orinski | |
| 10,471,273 B2 | 11/2019 | Segev et al. | |
| 10,644,194 B2 | 5/2020 | Kim et al. | |
| 10,814,140 B2 | 10/2020 | Zhang et al. | |
| 11,395,923 B2 | 7/2022 | Lu et al. | |
| 2002/0156513 A1 | 10/2002 | Borkan | |
| 2002/0161417 A1 | 10/2002 | Scribner | |
| 2004/0098063 A1 | 5/2004 | Goetz | |
| 2004/0147964 A1 | 7/2004 | Nolan et al. | |
| 2005/0216072 A1 | 9/2005 | Mahadevan-Jansen et al. | |
| 2006/0129210 A1 | 6/2006 | Cantin et al. | |
| 2006/0155348 A1 | 7/2006 | deCharms | |
| 2006/0161227 A1 | 7/2006 | Walsh, Jr. et al. | |
| 2007/0053996 A1 | 3/2007 | Boyden et al. | |
| 2007/0100398 A1 | 5/2007 | Sloan | |
| 2007/0150036 A1 | 6/2007 | Anderson | |
| 2007/0161919 A1 | 7/2007 | DiLorenzo | |
| 2007/0208395 A1 | 9/2007 | Leclerc et al. | |
| 2007/0244524 A1 | 10/2007 | Qu et al. | |
| 2007/0244526 A1 | 10/2007 | Zaghetto et al. | |
| 2008/0046053 A1 | 2/2008 | Wagner et al. | |
| 2008/0077198 A1 | 3/2008 | Webb et al. | |
| 2008/0146890 A1 | 6/2008 | LeBouef et al. | |
| 2008/0167701 A1 | 7/2008 | John et al. | |
| 2008/0197300 A1 | 8/2008 | Kayser et al. | |
| 2008/0243218 A1 | 10/2008 | Bottomley et al. | |
| 2009/0054954 A1 | 2/2009 | Foley et al. | |
| 2009/0054955 A1 | 2/2009 | Kopell et al. | |
| 2009/0069871 A1 | 3/2009 | Mahadevan-Jansen et al. | |
| 2009/0118800 A1 | 5/2009 | Deisseroth et al. | |
| 2009/0187222 A1 | 7/2009 | Barker | |
| 2009/0196471 A1 | 8/2009 | Goetz et al. | |
| 2009/0276021 A1 | 11/2009 | Meadows et al. | |
| 2009/0287272 A1 | 11/2009 | Kokones et al. | |
| 2009/0287273 A1 | 11/2009 | Carlton et al. | |
| 2009/0299447 A1 | 12/2009 | Jensen et al. | |
| 2010/0076508 A1 | 3/2010 | McDonald et al. | |
| 2010/0076535 A1 | 3/2010 | Pianca et al. | |
| 2010/0094364 A1 | 4/2010 | McDonald | |
| 2010/0105997 A1 | 4/2010 | Ecker et al. | |
| 2010/0114190 A1 | 5/2010 | Bendett et al. | |
| 2010/0174329 A1 | 7/2010 | Dadd et al. | |
| 2010/0174344 A1 | 7/2010 | Dadd et al. | |
| 2010/0256693 A1 | 10/2010 | McDonald et al. | |
| 2010/0268298 A1 | 10/2010 | Moffitt et al. | |
| 2010/0292758 A1 | 11/2010 | Lee et al. | |
| 2010/0292759 A1 | 11/2010 | Hahn et al. | |
| 2010/0324630 A1 | 12/2010 | Lee et al. | |
| 2010/0326701 A1 | 12/2010 | McDonald | |
| 2011/0004267 A1 | 1/2011 | Meadows | |
| 2011/0005069 A1 | 1/2011 | Pianca | |
| 2011/0009932 A1 | 1/2011 | McDonald et al. | |
| 2011/0022100 A1 | 1/2011 | Brase et al. | |
| 2011/0029055 A1 | 2/2011 | Tidemand | |
| 2011/0046432 A1 | 2/2011 | Simon et al. | |
| 2011/0046700 A1 | 2/2011 | McDonald et al. | |
| 2011/0078900 A1 | 4/2011 | Pianca et al. | |
| 2011/0106208 A1 | 5/2011 | Faltys et al. | |

(56) References Cited

U.S. PATENT DOCUMENTS

| | | |
|---|---|---|
| 2011/0112591 A1 | 5/2011 | Seymour et al. |
| 2011/0125077 A1 | 5/2011 | Denison et al. |
| 2011/0125078 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0172725 A1 | 7/2011 | Wells et al. |
| 2011/0238129 A1 | 9/2011 | Moffitt et al. |
| 2011/0295331 A1 | 12/2011 | Wells et al. |
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0029420 A1* | 2/2012 | Rittman, III ...... A61M 25/0043 604/20 |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0184794 A1 | 7/2013 | Feldman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0074182 A1 | 3/2014 | Wolf, II |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005680 A1 | 1/2015 | Lipani |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1 | 2/2015 | Goldman et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0080757 A1* | 3/2015 | Torisawa ............... A61B 1/31 600/560 |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1 | 10/2015 | Nielsen et al. |
| 2015/0360031 A1 | 12/2015 | Bornzin et al. |
| 2015/0375006 A1 | 12/2015 | Denison et al. |
| 2016/0030749 A1 | 2/2016 | Carcieri et al. |
| 2016/0045740 A1 | 2/2016 | Rezai et al. |
| 2016/0067519 A1 | 3/2016 | Tranberg et al. |
| 2016/0082251 A1 | 3/2016 | Moffitt et al. |
| 2016/0082253 A1 | 3/2016 | Moffitt et al. |
| 2016/0151639 A1 | 6/2016 | Scharf et al. |
| 2016/0228692 A1 | 8/2016 | Steinke et al. |
| 2016/0250474 A1 | 9/2016 | Stack et al. |
| 2016/0250497 A1 | 9/2016 | Jay |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0331994 A1 | 11/2016 | Smith et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0000419 A1 | 1/2017 | Schouenborg |
| 2017/0061627 A1 | 3/2017 | Bokil |
| 2017/0095670 A1 | 4/2017 | Ghaffari et al. |
| 2017/0100580 A1 | 4/2017 | Olson |
| 2017/0136254 A1 | 5/2017 | Simon et al. |
| 2017/0143985 A1 | 5/2017 | Degenaar et al. |
| 2017/0172446 A1 | 6/2017 | Kuzum et al. |
| 2017/0182191 A1 | 6/2017 | Towne et al. |
| 2017/0225007 A1 | 8/2017 | Orinski |
| 2017/0259078 A1 | 9/2017 | Howard |
| 2017/0281928 A1 | 10/2017 | Orinski |
| 2017/0281966 A1 | 10/2017 | Basiony |
| 2017/0304633 A1 | 10/2017 | Zhang |
| 2017/0348522 A1 | 12/2017 | Stoffregen et al. |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1* | 4/2018 | Serrano Carmona ........................ A61B 5/0084 |
| 2018/0154152 A1 | 6/2018 | Chabrol et al. |
| 2018/0193655 A1 | 7/2018 | Zhang et al. |
| 2018/0229042 A1 | 8/2018 | Kaula et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0326219 A1 | 11/2018 | Wolf, II |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0003898 A1 | 1/2019 | Dehkhoda et al. |
| 2019/0201709 A1 | 7/2019 | Tischendorf et al. |
| 2019/0209834 A1 | 7/2019 | Zhang et al. |
| 2019/0209849 A1 | 7/2019 | Hershey et al. |
| 2019/0209850 A1 | 7/2019 | Steinke |
| 2020/0001096 A1 | 1/2020 | Zhang et al. |
| 2020/0094047 A1* | 3/2020 | Govea ................. A61N 1/0504 |
| 2020/0155584 A1 | 5/2020 | DiMauro |
| 2020/0155854 A1 | 5/2020 | Even et al. |
| 2020/0271796 A1 | 8/2020 | Tahon et al. |
| 2020/0323589 A1 | 10/2020 | Varol |
| 2020/0376262 A1 | 12/2020 | Clark et al. |
| 2020/0376272 A1 | 12/2020 | Block et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2022/0054226 A1 | 2/2022 | Gregg, II et al. |
| 2022/0072329 A1 | 3/2022 | Howard |
| 2022/0339448 A1 | 10/2022 | Jayakumar et al. |
| 2024/0058619 A1 | 2/2024 | Zhu et al. |
| 2024/0198128 A1 | 6/2024 | Jenkins et al. |
| 2024/0226596 A1 | 7/2024 | Carbunaru et al. |

(56) References Cited

U.S. PATENT DOCUMENTS

FOREIGN PATENT DOCUMENTS

| WO | 02/091935 | 11/2002 |
|----|-----------|---------|
| WO | 2010029297 | 3/2010 |
| WO | 2011/031131 | 3/2011 |
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |
| WO | 2021141163 | 7/2021 |

OTHER PUBLICATIONS

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

R G Wilson, "Ball-lens coupling efficiency for laser-diode to single-mode fiber: comparison of independent studies by distinct methods," Applied Optics May 20, 1998, 37 (15): 3201-5.

International Search Report and Written Opinion for PCT Application No. PCT/US2022/023698 mailed Jul. 8, 2022.

U.S. Appl. No. 18/232,649, filed Aug. 10, 2023.

U.S. Appl. No. 18/232,621, filed Aug. 10, 2023.

Weiran Cao, Jian Li, Hongzheng Chen, Jiangeng Xue, "Transparent electrodes for organic optoelectronic devices: a review," J. Photon. Energy 4(1) 040990 (Oct. 30, 2014) https://doi.org/10.1117/1.JPE.4.040990.

Lee KT, Park DH, Baac HW, Han S. Graphene- and Carbon-Nanotube-Based Transparent Electrodes for Semitransparent Solar Cells. Materials (Basel). Aug. 22, 2018;11(9):1503. doi: 10.3390/ma11091503. PMID: 30135379; PMCID: PMC6165141.

\* cited by examiner

PHOTOBIOMODULATION SYSTEM AND DELIVERY DEVICE AND METHODS OF MAKING AND USING

CROSS-REFERENCE TO RELATED APPLICATIONS

This application claims the benefit under 35 U.S.C. § 119(e) of U.S. Provisional Patent Application Ser. No. 63/172,415, filed Apr. 8, 2021, which is incorporated herein by reference.

FIELD

The present disclosure is directed to the area of implantable photobiomodulation systems and delivery devices and methods of making and using the systems and devices. The present disclosure is also directed to implantable photobiomodulation systems that include an arrangement for delivery of medication or other materials.

BACKGROUND

Implantable systems for photobiomodulation (PBM) can also provide therapeutic benefits in a variety of diseases and disorders. A photobiomodulation system may include a control module with one or more light sources and, often, one or more optical fibers to carry the light to the desired photobiomodulation site. Photobiomodulation can produce a variety of effects including, but not limited to, stimulation, augmentation, inhibition, or the like or any combination thereof.

BRIEF SUMMARY

In one aspect, a photobiomodulation system includes a) a control module having a housing, an electronic subassembly disposed in the housing, a connector coupled or coupleable to the housing and defining a lead coupling end, a catheter coupling end, and a connector lumen extending from the lead coupling end to the catheter coupling end, and at least one light source electrically coupled to the electronic subassembly and configured to produce light in response to signals from the electronic subassembly; b) a lead coupled or coupleable to the control module and having a distal portion spaced apart from the control module, the lead having a lead body defining a lead lumen that is configured for positioning in fluid communication with the connector lumen of the connector of the control module, the lead body further defining at least one opening along the distal portion of the lead and in fluid communication with the lead lumen, a plurality of light emitters arranged along the distal portion of the lead, and a plurality of optical fibers extending along the lead body and coupled to the light emitters and configured to receive light from the at least one light source and deliver the light to the light emitters; and c) a catheter assembly having a tube coupleable to a catheter pump, and a distal connector attached to an end of the tube and coupled or coupleable to the catheter coupling end of the connector of the control module, the distal connector including an assembly lumen extending from the tube and configured for fluid communication with the connector lumen of the connector of the connector of the control module.

In at least some aspects, the at least one light source is a plurality of light sources disposed in a radial arrangement. In at least some aspects, the light emitters are disposed in a radial arrangement. In at least some aspects, the photobiomodulation further includes an imaging device disposed on the distal portion of the lead. In at least some aspects, the connector of the control module further includes electrical contacts and the lead includes conductors coupled to the imaging device and configured for electrically coupling the electrical contacts.

In at least some aspects, the photobiomodulation further includes the catheter assembly further includes the catheter pump. In at least some aspects, the distal connector includes a needle defining a portion the assembly lumen. In at least some aspects, either the connector or the lead body includes a septum disposed in the connector lumen or the lead lumen, respectively.

In at least some aspects, the photobiomodulation system further includes a coupling arrangement for coupling the distal connector of the catheter assembly to the catheter coupling end of the connector. In at least some aspects, the connector is detachable from the housing. In at least some aspects, the connector further includes at least one cylindrical lens to receive the light from the at least one light source.

In at least some aspects, the control module further includes a power source disposed in the housing and coupled to the electronic subassembly. In at least some aspects, the connector of the control module further includes one or more seals disposed within or adjacent at least one of the catheter coupling end or the lead coupling end to hinder flow of fluid past the one or more seals. In at least some aspects, the photobiomodulation system further includes a programming unit configured to communicate with the electronic subassembly of the control module. In at least some aspects, the photobiomodulation system further includes an imaging device disposed on the distal portion of the lead, wherein the programming unit is configured to display images from the imaging device.

Another aspect is a delivery tool for delivery of the lead of any of the photobiomodulation systems described above. The delivery tool includes a hand grip arrangement; a barrel attached to the hand grip arrangement; a scissor grip for gripping the lead, the scissor grip extending out of the barrel and operatively coupled to the hand grip arrangement, wherein operation of the hand grip arrangement opens and closes the scissor grip; and a vertical steering mechanism extending from the barrel and coupled to the scissor grip to move the scissor grip up and down relative to the barrel without opening or closing the scissor grip.

In at least some aspects, the vertical steering mechanism includes a steering disc, at least one tab extending from the steering disc for rotating the steering disc relative to the barrel, and steering cables attached to, and extending between, the steering disc and scissor grip.

A further aspect is a method of implanting the lead of any of the photobiomodulation systems described above. The method includes holding the distal portion of the lead using a delivery tool; inserting the delivery tool into the patient; guiding the delivery tool and lead to the site of photobiomodulation; and releasing the distal portion of the lead from the delivery tool.

In at least some aspects, the lead further includes an imaging device disposed on the distal portion of the lead, wherein guiding and lead the delivery tool includes receiving images from the imaging device to guide the delivery tool and lead to the site of photobiomodulation. In at least some aspects, the delivery tool includes a vertical steering mechanism to move a grip of the delivery tool up or down, wherein guiding the delivery tool and lead includes using the vertical steering mechanism to facilitate guidance of the delivery tool and lead to the site of photobiomodulation.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable photobiomodulation systems and delivery devices and methods of making and using the systems and devices. The present disclosure is also directed to implantable photobiomodulation systems that include an arrangement for delivery of medication or other materials.

Photobiomodulation (PBM) can be used to produce effects in the tissue of a patient including, but not limited to, stimulation, augmentation, inhibition, or the like or any combination thereof. PBM can be used to provide treatment for variety of diseases and disorders depending, at least in part, on the site of implantation and the wavelength(s) of light delivered. Photobiomodulation may include, but is not necessarily limited to, stimulation or other effects resulting from response to particular wavelengths or wavelength ranges of light or from thermal effects generated using light or any combination thereof.

As an example, for treatment of diabetes, it is believed that insulin production can be augmented by the application of PBM therapy to β-cells, such as β-cells found in the islets of Langerhans in the pancreas. Exocytosis of the β-cells is dependent on mitochondria production of ATP. It is believed that PBM therapy can increase the performance of the mitochondria in the β-cells to increase ATP production which can depolarize the cell membrane to allow calcium ions to pass through the cell membrane initiating exocytosis and the release of insulin from the β-cells.

Figure 1:
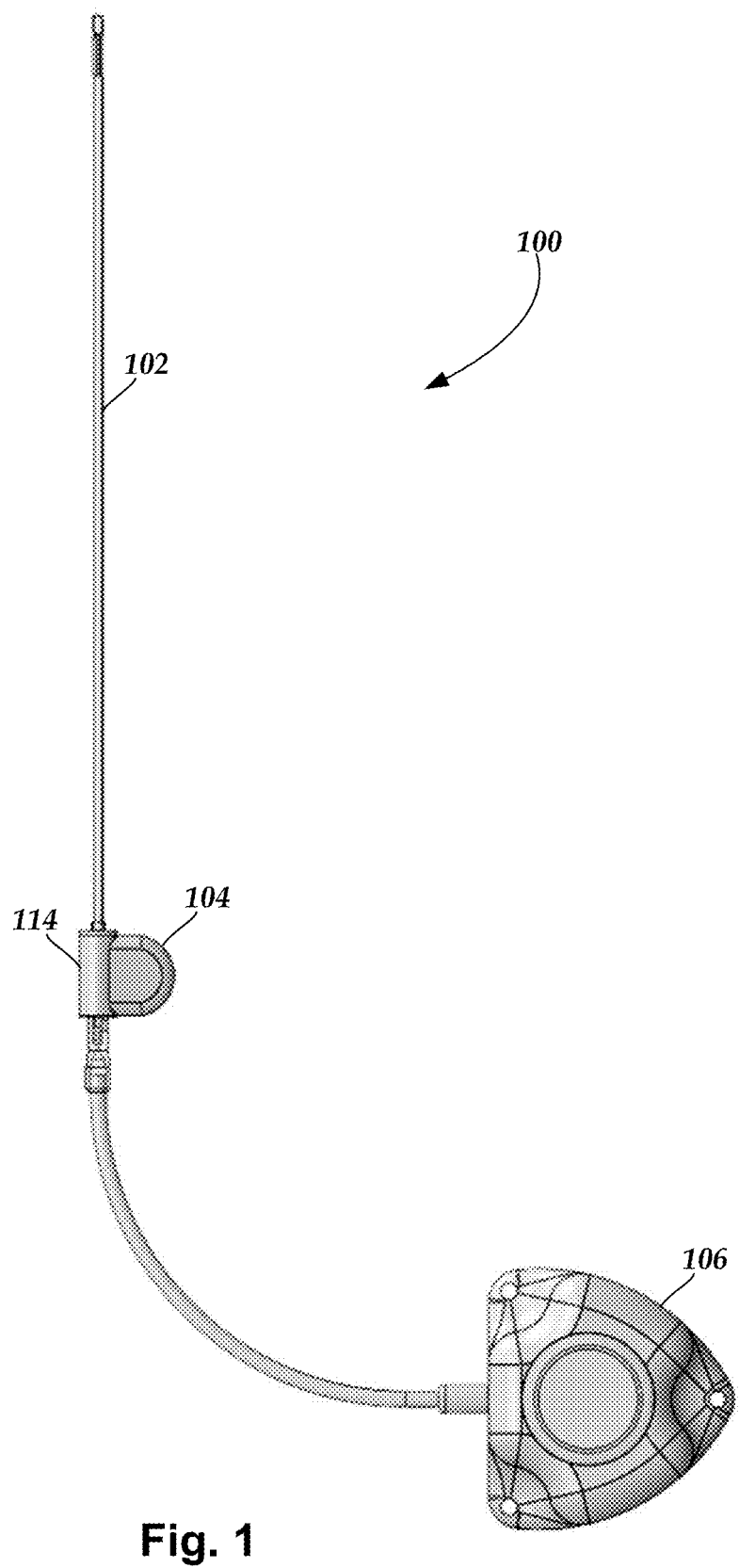
FIG. 1 is a schematic side view of one embodiment of a photobiomodulation system.

FIG. 1 is a schematic side view of one embodiment of a photobiomodulation (PBM) system 100. The PBM system 100 includes a lead 102, a control module (or implantable pulse generator (IPG)) 104, and a catheter assembly 106. In at least some embodiments, the lead 102 is permanently coupled to the control module 104 (or a portion of the control module such as a connector 114.) In at least some embodiments, one or both of the lead 102 or catheter assembly 106 is detachable from the control module 104.

Figure 2A:
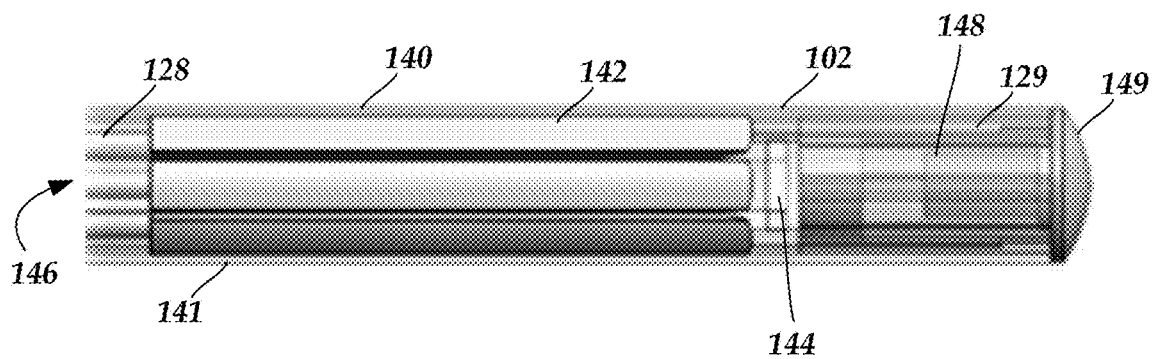
FIG. 2A is a schematic side view of one embodiment of a distal portion of a lead of the photobiomodulation system of FIG. 1.
Figure 2B:
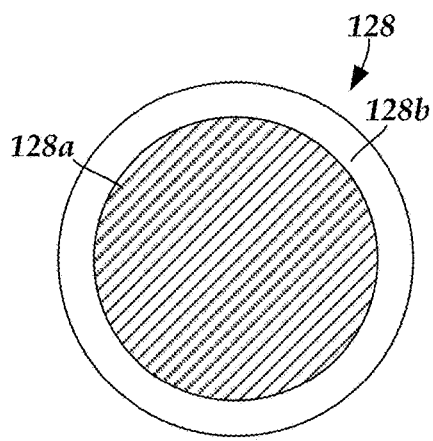
FIG. 2B is a schematic cross-sectional view of one embodiment of an optical fiber of the lead of FIG. 2A.

The lead 102 extends from the control module 104. FIG. 2A illustrates a distal portion 140 of the lead 102. The lead 102 includes a lead body 141 (which has been made partially transparent in FIG. 2A to allow viewing of other elements of the lead) and multiple optical fibers 128 that extend along the lead and terminate in optical emitters 142. Any suitable optical fibers 128 can be used. The terms "optical fiber" and "fiber optic" are used interchangeably herein and can be any suitable light guides or waveguides. As illustrated in FIG. 2B, an optical fiber 128 can include a core 128a and a cladding 128b. The core 128a of an optical fiber 128 can be made of, for example, glass, polymer (such as silicone), or any other suitable material. The cladding 128b can also be made of any suitable material including, but not limited to, polymers such as fluoropolymers. In at least some embodiments, the lead body 141, or a portion of the lead body, may act as the cladding 128b.

In general, the cladding 128b of the optical fiber 128 has an index of refraction, n, (for at least one or more wavelengths of light that are to be transmitted along the optical fibers 128) that is less than the index of refraction, $n_{core}$, of the core 128a ($n<n_{core}$). Light transmitted along the core 128a is reflected at the barrier between the core and cladding 128b if the angle of incidence, θ, is less than a critical angle ($\theta_c = \sin^{-1}(n/n_{core})$). In at least some embodiments, the optical fibers 128 have a critical angle of at least 60, 65, or 70 degrees. In at least some embodiments, the optical fibers 128 have an acceptance angle of at least 15 or 20 degrees.

Returning to FIG. 2A, the optical emitters 142 can be portions of the optical fibers 128 or can be attached to the optical fibers. For example, the optical emitters 142 can be portions of the optical fibers 128 from which the cladding 128b has been removed or can be made of the same or similar material to the core (or any other suitable material) with no cladding. Examples of optical emitters can be found in U.S. Patent Application Publication 2020/0155854, incorporated herein by reference in its entirety.

In at least some embodiments, the optical emitters 142 are not covered by the lead body 141. In other embodiments, the optical emitters 142 may be covered by the lead body 141 and, at least the portion covering the optical emitters, is made of material that is transparent or translucent to the light emitted from the optical emitters. In some embodiments, the lead body 141, or one or more separate optical elements disposed on the optical emitters 142 or the optical emitter 128 itself, may include a lens, diffuser (for example, a defusing material or particles or a roughened surface of the optical emitter), polarizer, or other optical element at positions from which light can be emitted from the optical emitters.

Any suitable number of optical emitters 142 can be used including, but not limited to, one, two, three, four, five, six, eight, ten, twelve, or more. In at least some embodiments with multiple optical emitters 142, the optical emitters 142 are disposed in a radial arrangement around the lead 102, as illustrated in FIG. 2A. Any other suitable arrangement can also be used. In at least some embodiments, at last some of the optical emitters 142 may also or alternatively be arranged in a longitudinal arrangement along the length of the lead 102. The radial or longitudinal (or both) arrangement of the optical emitters 142 can facilitate directional application of light to the tissue in which the lead 102 is implanted. In at least some embodiments, the optical emitters 128 have a length of at least 0.5, 1, 2, 3, 4, or 5 mm or longer. In at least some embodiments, the optical emitters 128 have a width of no more than 2, 1, 0.5, or 0.3 mm.

The lead 102 also includes a lumen 146, defined by the lead body 141, that extends from the proximal portion of the lead to one or more openings 144 for flow of fluid, such as medications, water, or saline, from the catheter assembly 106 along the lead 102 and out the openings 144. (In at least some embodiments, the openings 144 and lumen 146 can be used to draw out fluids, such as blood or other bodily fluids from the tissue.)

Figure 2C:
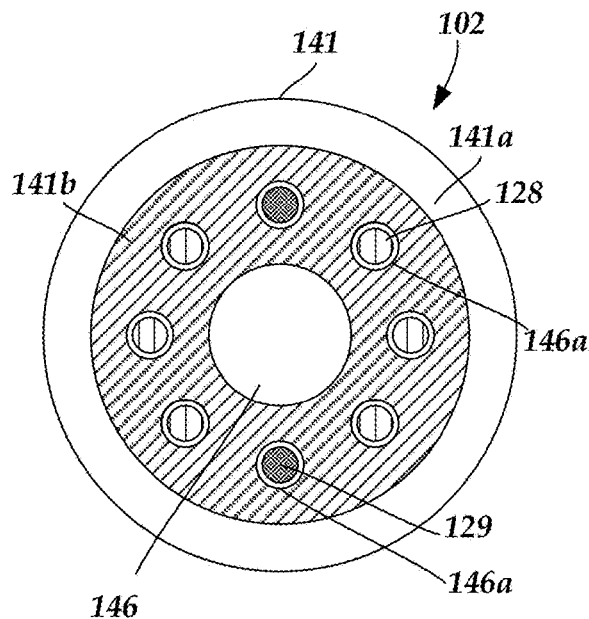
FIG. 2C is a schematic cross-sectional view of a portion of the lead of the photobiomodulation system of FIG. 1.

In at least some embodiments, as illustrated in FIG. 2C, the lumen 146 is a central lumen with one or more additional lumens 146a defined in the lead body for passage of the optical fibers 128 and conductors 129, such as wires or traces, for the imaging device 148, as described below. In at least some embodiments, the lead body 141 can define individual additional lumens for each of the optical fibers 128 and conductors 129. In other embodiments, a lumen can include two or more of the optical fibers 128 or conductors 129. Yet other embodiments can include any other suitable arrangement of the lead body 141, lumen 146, optical fibers 128, and conductors 129.

In at least some embodiments, the lead body 141 includes a jacket 141a and a multi-lumen guide 141b. The jacket 141a and multi-lumen guide 141b can be made of any suitable material, such as, for example, polymeric materials such as silicone or polyurethane or the like or any combination thereof. The jacket 141a and multi-lumen guide 141b can be made of the same or different materials. In other embodiments, the lead body 141 only includes the multi-lumen guide 141b.

The distal portion 140 of the lead 102 optionally includes an imaging device 148, such as a camera, to aid in implantation or observation of the treatment site. Conductors 129 extend along the lead 102 to provide power to the imaging device 148 and may conduct signals from the imaging device. In other embodiments, the imaging device 148 or lead 102 can include an antenna to transmit the signals from the imaging device to a viewing device (for example, a programming device) using any suitable transmission technique. In at least some embodiments, the proximal end of the lead 102 may include contacts 143 (FIG. 3A) that are attached to the conductors 129 and arranged to couple to the electrical contacts 116 of the control module 104.

The imaging device 148 can be front-facing, side-facing, or any combination thereof. In at least some embodiments, the imaging device 148 has a field of view of at least 90, 100, 120, 140, or more degrees. In at least some embodiments, a lens 149 or other optical element(s) is disposed on the distal end of the lead 102. One example of a suitable imaging device is a camera, such as the CameraCubeChip™ from OmniVision (Santa Clara, CA, USA). Any other suitable camera or other imaging device (for example, an ultrasound imaging device) can be used.

In at least some embodiments, an optical emitter or a light source (such as a laser diode, light emitting diode (LED), organic light emitting diode (OLED), or vertical cavity side-emitting laser (VCSEL)) may be disposed at the tip of the lead 102 near the imaging device 148 to emit light from through the tip (for example, through the lens 149). Design considerations for this optical emitter or light source can be the same as those for the optical emitters 142 or light sources 118.

Figure 3A:
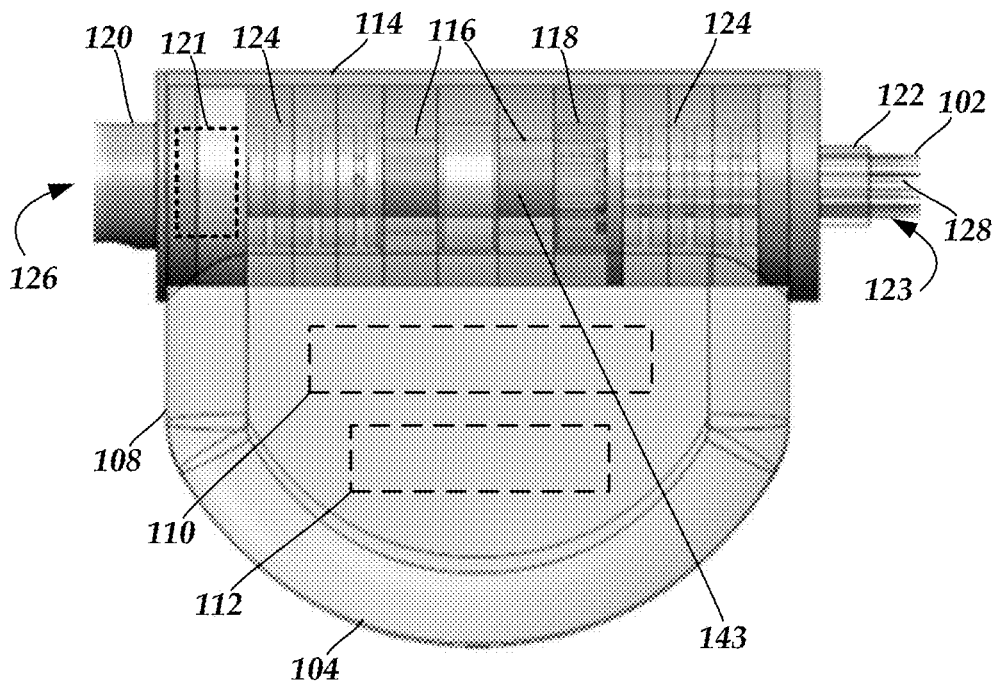
FIG. 3A is a schematic side view of one embodiment of a control module and a proximal portion of a lead of the photobiomodulation system of FIG. 1.

FIG. 3A illustrates one embodiment of the control module 104 that includes a housing 108 with an electronic subassembly 110 and an optional power source 112 disposed in the housing. Preferably, the housing 108 is hermetically sealed.

The control module 104 also includes a connector 114 with electrical contacts 116, one or more light sources 118, a catheter coupling end 120 for coupling to the catheter assembly 106, and a lead coupling end 122 for coupling to the lead 102. In at least some embodiments, the lead 102 is permanently coupled to the connector 114. In other embodiments, the lead 102 is arranged for removably coupling to the connector. The lead coupling end 122 includes a port 123 for receiving a portion of the lead 102, as illustrated in FIG. 3A. If the lead 102 is removably coupleable, the lead 102 and lead coupling end 122 can include a coupling mechanism for coupling the proximal end of the lead to the lead coupling end. For example, the coupling mechanism can include a threaded opening in the lead coupling end 122 and a set screw that is screwed down against the lead 102. Other coupling mechanism include twist couplings, screw-on couplings, push on couplings, or the like or any combination thereof.

In at least some embodiments, the connector 114 is part of the housing 108 and the electronic subassembly 110 and the optional power source 112 are coupled to the electrical contacts 116 and one or more light sources 118 using conductors (not shown), such as wires or traces.

In other embodiments, the connector 114 is permanently or removably attached to the housing 108. In at least some embodiments, the connector 114 may be permanently attached to the lead 102 instead of the housing 108 of the control module 104. In at least some embodiments, the connector 114 may be removably attached or attachable to the housing 108 using any suitable attachment mechanism. In at least some embodiments, when attached, the connector 114 is rotatably locked to the housing 108.

Figure 3B:
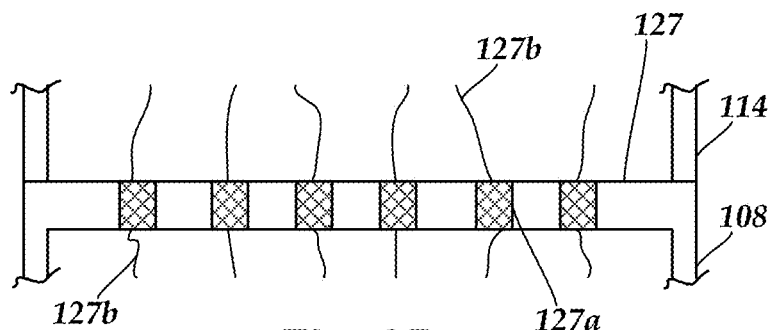
FIG. 3B is a schematic cross-sectional view of a feedthrough interface between a housing and a connector of the control module of FIG. 3A.

In at least some embodiments, as illustrated in FIG. 3B, the housing 108 can include a feedthrough 127 with feedthrough pins 127a to couple the electronic subassembly 110 and the optional power source 112 within the housing to the electrical contacts 116 and one or more light sources 118 of the connector using conductors 127b, such as wires or traces.

Returning to FIG. 3A, the connector 114 of the control module 104 preferably includes one or more seals 124 within, or adjacent to, the catheter and lead coupling ends 120, 122 to hinder or prevent inflow of fluid to the region of the connector 106 containing the electrical contacts 116 and one or more light sources 118. If the lead 102 is permanently coupled to the connector 114, then the conductors 129 of the lead can be attached to the electrical contacts 116. If the lead 102 is removable from the connector 114, the lead can include contacts 143 on the proximal end of the lead which are attached to the conductors 129 and arranged to contact the electrical contacts 116 when the lead is inserted into the port 123 of the connector 114.

The control module 104 further defines a lumen 126 that extends from the catheter coupling end 120 to the lead coupling end 122. The lumen 126 may be arranged to receive a proximal portion of the lead 102. The lumen 126 may be arranged to allow for flow of fluid from the catheter assembly 104, through the connector 114, to the lumen 146 of the lead 102. In at least some embodiments, at the catheter coupling end 120, the lumen 126 can have a septum 121. In other embodiments, the lumen 146 of the lead 102 can include the septum 121.

The one or more light sources 118 can be, for example, laser diodes, light emitting diodes (LEDs), organic light emitting diodes (OLEDs), vertical cavity side-emitting lasers (VCSELs), lamps, or any other suitable light source. The one or more light sources 118 are electrically coupled to electronic subassembly 110 and power source 112. Any number of light sources 118 can be used including, but not limited to, one, two, three, four, five, six, eight, ten, twelve, or more light sources. In at least some embodiments with multiple light sources 118, the light sources are arranged radially within the connector 114. Any other suitable arrangement of the light sources can be used.

In at least some embodiments, the number of light sources 118 is equal to the number of light emitters 142 (FIG. 2) on the lead 102 with each light source coupled to one of the light emitters. In at least some embodiments, such an arrangement allows for independent operation of each of the light emitters 142 (FIG. 2). In other embodiments, a light source 118 may be coupled to two or more of the light emitters 142 (FIG. 2).

The light source(s) 118 can be selected to produce any suitable wavelength(s) of light including one or more wavelengths of visible, infrared, or ultraviolet light. In at least some embodiments, the light sources produce light in a wavelength range of 640 to 680 or in a range from 780 to 820 or in any combination thereof. In at least some embodiments, the light sources 118 produce the same wavelength(s) of light. In other embodiments, different light sources 118 may be used to produce different wavelengths of light. In at least some embodiments, each light emitter 142 (FIG. 2) is coupled to two or more light sources 118 that produce different wavelengths of light. In at least some embodiments, the light source(s) 118 may include optical elements, such as filters, polarizers, lenses, collimators, or the like or any combination thereof to alter or modify the light emitted from the light source(s).

The one or more light sources 118 generate light based on programming of the control module 104 as implemented in the electronic subassembly 110. In at least some embodiments, the light source(s) 118 can be individually programmed. In at least some embodiments, the light emitted by each of the individual light emitters 128 can be individually programmed.

Figure 3C:
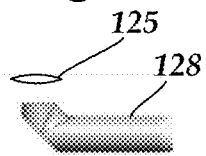
FIG. 3C is a schematic side view of a lens and an optical fiber of the photobiomodulation system of FIG. 1.

In at least some embodiments, the light from the light source(s) 118 is directed using one or more lenses 125 (for example, a converging lens as illustrated in FIG. 3C) or other optics to one or more optical fibers 128 of the lead 102 (or optical fibers in the connector 114 that are configured to transfer the light to the optical fibers 128 of the lead 102.) In at least some embodiments, lens(es) 125 facilitate directing the light toward the optical fiber(s) 128 within the acceptance angle of the optical fiber(s). In at least some embodiments, the lens(es) 125 are coupled to the optical fiber(s) 128. In at least some embodiments, multiple lenses may be used including a collimating lens and a converging lens.

If the lead 102 is permanently coupled to the connector 114, the optical fiber(s) 128 are permanently aligned with the light source(s) 118. If the lead 102 is removable from the connector 114, the lead 102 and connector 114 may have a shape or include an arrangement (such as a pin or ridge and corresponding groove) that restricts coupling of the lead 102 and connector 114 to one or more specific alignments, thereby aligning the optical fiber(s) 128 with the light source(s) 118.

Figure 4A:
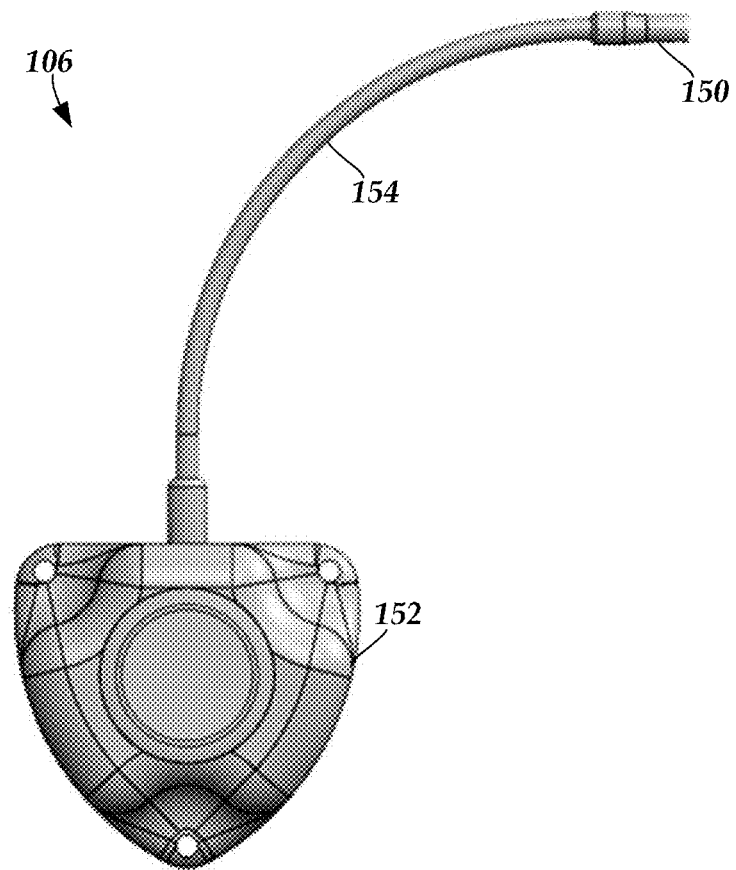
FIG. 4A is a schematic side view of one embodiment of a catheter assembly of the photobiomodulation system of FIG. 1.
Figure 4B:
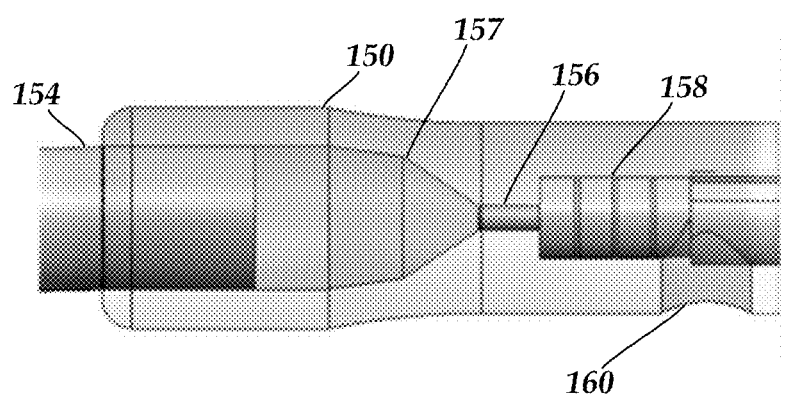
FIG. 4B is a schematic side view of one embodiment of distal connector of the catheter assembly of FIG. 4A.

FIG. 4A illustrates one embodiment of the catheter assembly 106 and FIG. 4B is a closer view of a distal connector 150 of the catheter assembly 106. The catheter assembly 106 includes a catheter pump 152, a tube 154 extending from the catheter pump, and the distal connector 150 coupled to the end of the tube. In at least some embodiments, the catheter pump 152 includes a pump and a reservoir to hold the medication or other fluid for pumping. In at least some embodiments, the catheter pump 152 can be decoupled from the tube 154.

In at least some embodiments, the distal connector 150 defines an assembly lumen 157 that extends from the tube 154 and includes a needle 156 that is arranged for insertion into the lumen 126 of the control module 104 (or the lumen 146 of the lead 102 if the lead 102 extends to the catheter coupling end 120 of the control module) when the catheter assembly 106 is coupled to the control module. In at least some embodiments, the lumen 126 of the control module 104 or the lumen 146 of the lead 102 includes a septum 121 that can be penetrated by the needle 156 for delivery of fluid. In at least some embodiments, the distal connector 150 includes sealing members 158 (for example, O-rings) around a portion of the needle 156 to prevent or hinder backflow of fluid into the distal connector 150.

In at least some embodiments, the distal connector 150 and catheter coupling end 120 include a coupling mechanism 160 for coupling the distal connector to the catheter coupling end. For example, the coupling mechanism can include a threaded opening in the distal connector 150 and a set screw that is screwed down against the catheter coupling end. Other coupling mechanisms include twist couplings, screw-on couplings, push on couplings, or the like or any combination thereof.

In at least some embodiments, the photobiomodulation system 100 includes one or more of the following: a) the ability to administer medication or other fluids at the photobiomodulation site; b) real time visualization during or after implantation; or c) radial distribution and control of the emitted light.

Figure 5A:
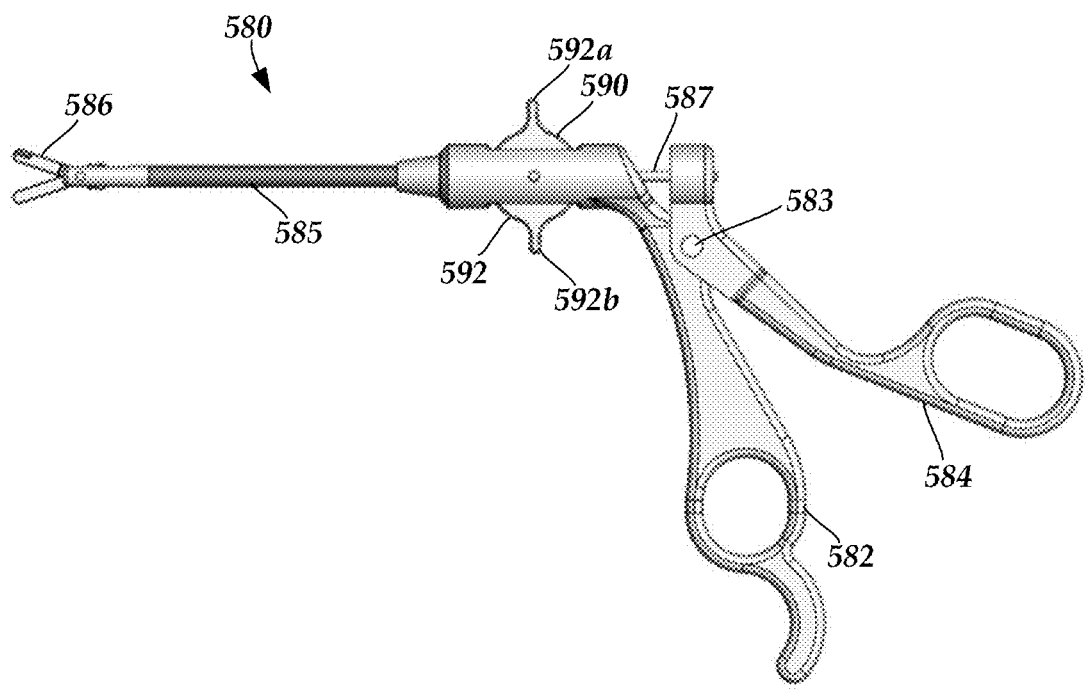
FIG. 5A is a schematic side view of one embodiment of a delivery tool.
Figure 5B:
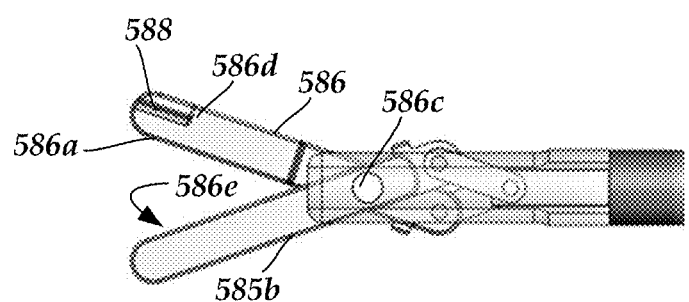
FIG. 5B is a schematic side close-up view of one embodiment of a scissor grip and barrel of the delivery tool of FIG. 5A.

FIG. 5A illustrates one embodiment of a delivery tool 580 for delivery of the lead 102 to a site for photobiomodulation. The delivery tool 580 includes an ergonomic hand grip arrangement having a first grip 582 and second grip 584 that is pivotably attached to the first grip 582 at a pivot point 583. The delivery tool 580 also includes a barrel 585 extending from the first grip 582 and a scissor grip 586 extending out of the barrel. The scissor grip 586 has a first scissor arm 586*a* and a second scissor arm 586*b* that are pivotable relative to each other at a pivot point 586*c*, as illustrated in the close-up view of FIG. 5B. The second grip 584 is coupled to the scissor grip 586 through a pull rod or cable 587. Moving the second grip 584 relative to the first grip 582 pushes or pulls the pull rod or cable 587 to open (FIGS. 5A and 5B) or close (FIG. 5C) the scissor grip 586. The facing interior surfaces 586*d*, 586*e* of the first and second scissor arms 586*a*, 586*b* each include a ridge or detent 588 that, when the scissor grip 586 is closed, bound the lead 102 to hold the lead within the scissor grip 586.

Figure 5C:
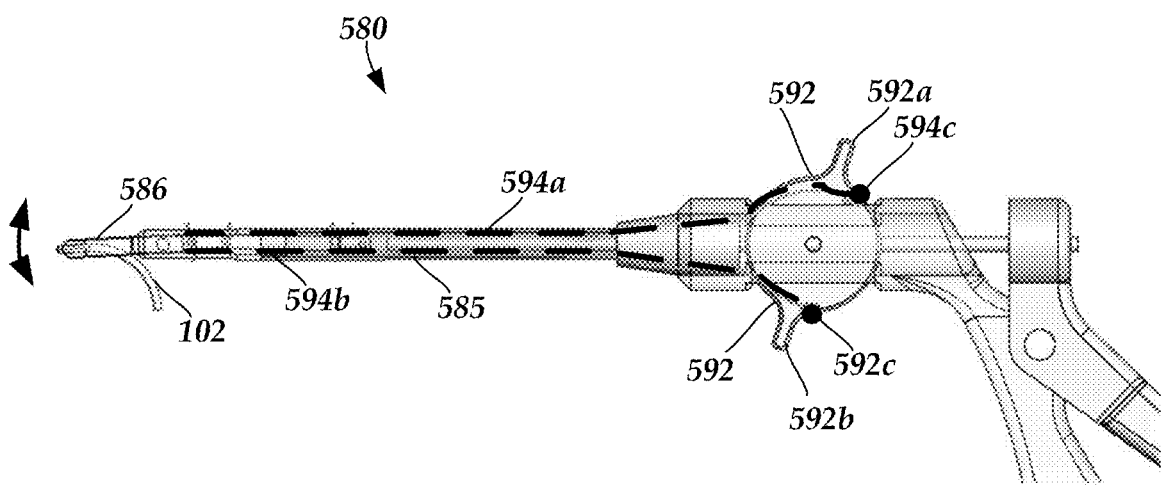
FIG. 5C is a schematic side close-up view highlighting one embodiment of a vertical steering mechanism of the delivery tool of FIG. 5A.

In at least some embodiments, the delivery tool 580 also includes a vertical steering mechanism 590 that can be used to move the scissor grip 586, and any lead 102 held by the scissor grip, up or down relative to the barrel 585. The vertical steering mechanism 590 includes a vertical steering disc 592, tabs 592*a*, 592*b* extending from the vertical steering disc for manipulation by the user, and, as illustrated in FIG. 5C, two steering cables 594*a*, 594*b* that are attached to the vertical steering disc or tabs and to opposing sides of the scissor grip 586. The user moves manipulates the tabs 592*a*, 592*b* to pull on one of the steering cables 594*a*, 594*b* to move the scissor grip 586, and any lead 102 held by the scissor grip, up or down relative to the barrel 585. This vertical motion can facilitate more precise delivery or implantation of the lead 102 at the desired implantation site. In at least some embodiments, the imaging device 148 can be used to view the tissue in front or to the side of the lead 102 so that the user can guide the lead to the desired implantation site.

Figure 5D:
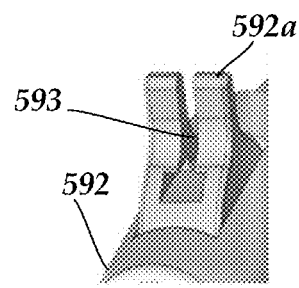
FIG. 5D is a schematic perspective close-up view of one embodiment of a tab of the vertical steering mechanism of the delivery tool of FIG. 5A.

In at least some embodiments, as illustrated in FIG. 5D, each of the tabs (e.g., tab 592*a*) includes a cut 593 that the steering cable (e.g., steering cable 594*a*) can fit within. As illustrated in FIG. 5C, each of the steering cables 594*a*, 594*b* can include a knot or other element 594*c* that is larger than the cut 593 so that the steering cable is fixed to the tab 592*a*, 592*b*.

In at least some embodiments, the delivery tool 580 can provide for accurate and precise delivery of the lead 102 to the desired photobiomodulation site. This may be particularly important in regions, such as near the pancreas, where organ or tissue damage may have dangerous consequences.

Although the leads described above provide photobiomodulation, it will be understood that the leads, systems, arrangements, and methods can be modified to provide photobiomodulation and electrical stimulation by, for example, including components, such as electrodes or elements that provide current to the electrodes, for electrical stimulation.

Examples of electrical stimulation systems with leads that can be modified to include the photobiomodulation system 100 are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 6:
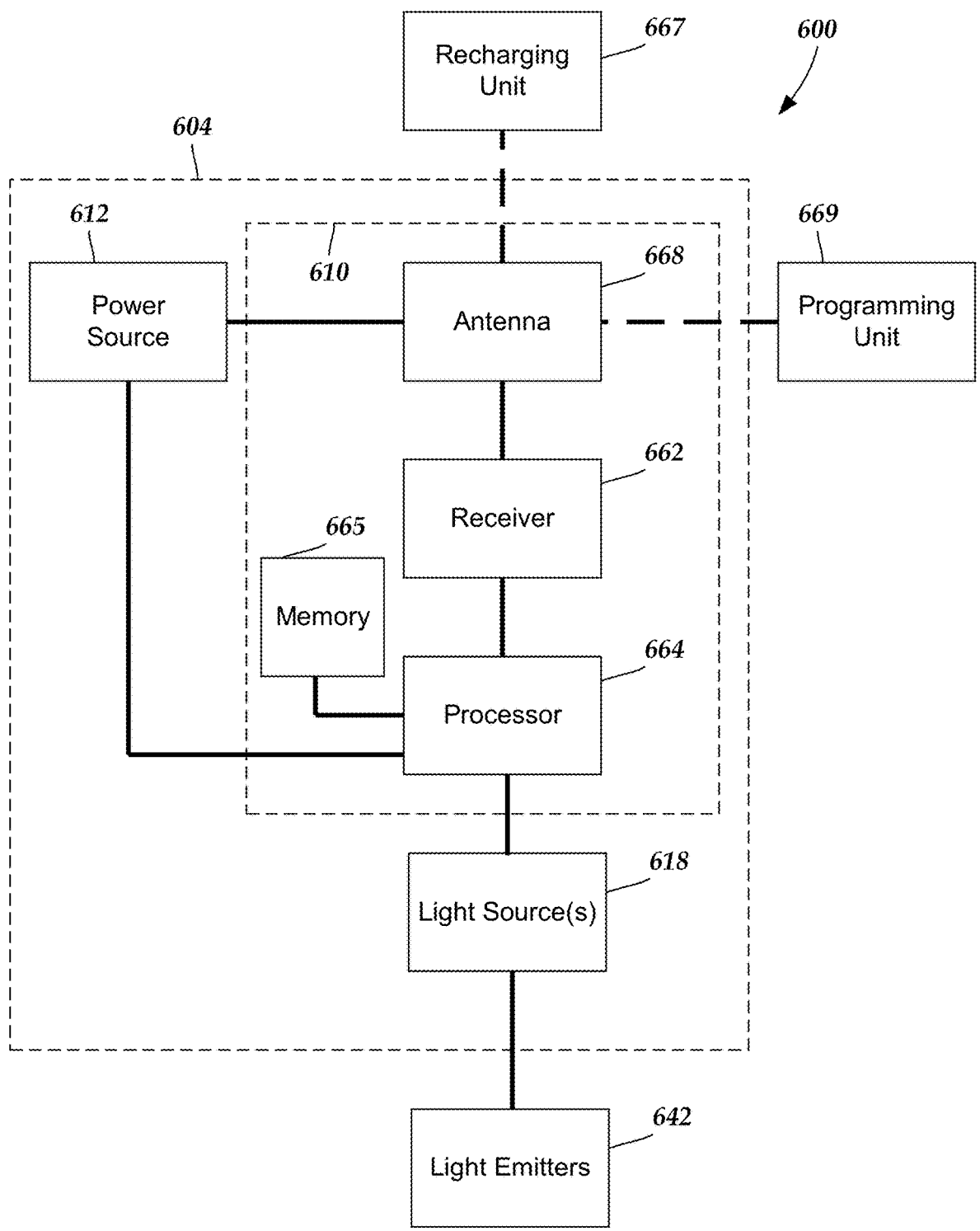
FIG. 6 is a block diagram of one embodiment of a system for photobiomodulation.

FIG. 6 is a schematic overview of one embodiment of components of a photobiomodulation system 600 including an electronic subassembly 610 disposed within a control module 664 (for example, an implantable pulse generator). It will be understood that the photobiomodulation system can include more, fewer, or different components and can have a variety of different configurations including those configurations disclosed in the stimulator references cited herein.

In at least some embodiments, selected components (for example, a power source 612, an antenna 668, a receiver 662, a processor 664, and a memory 665) of the photobiomodulation system can be positioned on one or more circuit boards or similar carriers within a sealed housing 108 (FIG. 2A) of a control module 604. Any suitable processor 664 can be used and can be as simple as an electronic device that, for example, produces signals to direct or generate photobiomodulation at a regular interval or the processor can be capable of receiving and interpreting instructions from an external programming unit 669 that, for example, allows modification of photobiomodulation parameters or characteristics.

The processor 664 is coupled to one or more light sources 618 which provide light to one or more light emitters 642, as described above. The processor 664 is generally included to control the timing and other characteristics of the photobiomodulation system. For example, the processor 664 can, if desired, control one or more of the timing, pulse frequency, amplitude, and duration of the photobiomodulation. In addition, the processor 664 can select one or more of the light sources 681 or light emitters 642 to provide photobiomodulation, if desired. In some embodiments, the processor 664 selects the frequency of the light for the photobiomodulation.

Any suitable memory 665 can be used. The memory 665 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, magnetic storage devices, or any other medium which can be used to store the desired information and which can be accessed by a processor.

Any power source 612 can be used including, for example, a battery such as a primary battery or a rechargeable battery. Examples of other power sources include super capacitors, nuclear or atomic batteries, fuel cells, mechanical resonators, infrared collectors, flexural powered energy sources, thermally-powered energy sources, bioenergy power sources, bioelectric cells, osmotic pressure pumps, and the like. As another alternative, power can be supplied by an external power source through inductive coupling via an antenna 668 or a secondary antenna. The external power source can be in a device that is mounted on the skin of the user or in a unit that is provided near the user on a permanent or periodic basis. In at least some embodiments, if the power source 612 is a rechargeable battery, the battery may be recharged using the antenna 668 and a recharging unit 667. In some embodiments, power can be provided to the power source for recharging by inductively coupling the power source 612 to the external recharging unit 667.

In at least some embodiments, the processor 664 is coupled to a receiver 662 which, in turn, is coupled to an antenna 668. This allows the processor 664 to receive instructions from an external source, such as a programming unit 669, to, for example, program the photobiomodulation parameters and characteristics. The signals sent to the processor 664 via the antenna 668 and the receiver 662 can be used to modify or otherwise direct the operation of the photobiomodulation system. For example, the signals may be used to modify the characteristics of the photobiomodulation system such as modifying one or more of timing, pulse frequency, amplitude, and duration of the photobiomodulation. The signals may also direct the photobiomodulation system 600 to cease operation, to start operation, to start charging the battery, or to stop charging the battery. In other embodiments, the photobiomodulation system does not include the antenna 668 or receiver 662 and the processor 664 operates as initially programmed.

In at least some embodiments, the antenna 668 is capable of receiving signals (e.g., RF signals) from an external programming unit 669 (such as a clinician programmer or patient remote control or any other device) which can be programmed by a user, a clinician, or other individual. The programming unit 669 can be any unit that can provide information or instructions to the photobiomodulation system 600. In at least some embodiments, the programming unit 669 can provide signals or information to the processor 664 via a wireless or wired connection. One example of a suitable programming unit is a clinician programmer or other computer operated by a clinician or other user to select, set, or program operational parameters for the photobiomodulation. Another example of the programming unit 669 is a remote control such as, for example, a device that is worn on the skin of the user or can be carried by the user and can have a form similar to a pager, cellular phone, or remote control, if desired. In at least some embodiments, a remote control used by a patient may have fewer options or capabilities for altering photobiomodulation parameters than a clinician programmer.

Optionally, the photobiomodulation system 600 may include a transmitter (not shown) coupled to the processor 664 and the antenna 668 for transmitting signals back to the programming unit 669 or another unit capable of receiving the signals. For example, the photobiomodulation system 600 may transmit signals indicating whether the photobiomodulation system 600 is operating properly or not or indicating when the battery needs to be charged or the level of charge remaining in the battery. The photobiomodulation system 600 may also transmit signals from the imaging device 148 (FIG. 2A) for viewing on the programming unit 669 or other device. The processor 664 may also be capable of transmitting information about the photobiomodulation characteristics so that a user or clinician can determine or verify the characteristics.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A photobiomodulation system, comprising:
   a control module implantable in a patient, the control module comprising
      a housing,
      an electronic subassembly disposed in the housing,
      a connector coupled or coupleable to the housing and defining a lead coupling end, a catheter coupling end, a connector lumen extending from the lead coupling end to the catheter coupling end, and a septum disposed in the connector lumen, and
      at least one light source electrically coupled to the electronic subassembly and configured to produce light in response to signals from the electronic subassembly;
   a lead implantable in the patient, coupled or coupleable to the control module, and having a distal portion spaced apart from the control module, the lead comprising
      a lead body defining a lead lumen that is configured for positioning in fluid communication with the connector lumen of the connector of the control module, the lead body further defining at least one opening along the distal portion of the lead and in fluid communication with the lead lumen,
      a plurality of light emitters arranged along the distal portion of the lead, and
      a plurality of optical fibers extending along the lead body and coupled to the light emitters and configured to receive light from the at least one light source and deliver the light to the light emitters; and
   a catheter assembly, comprising
      a tube coupleable to a catheter pump, and
      a distal connector attached to an end of the tube and coupled or coupleable to the catheter coupling end of the connector of the control module, the distal connector comprising an assembly lumen extending from the tube and configured for fluid communication with the connector lumen of the connector of the control module and a needle defining a portion of the assembly lumen and configured for penetrating the septum disposed in the connector lumen as the catheter assembly is coupled to the catheter coupling end of the connector of the control module.

2. The photobiomodulation system of claim 1, wherein the at least one light source is a plurality of light sources disposed in a radial arrangement.

3. The photobiomodulation system of claim 1, wherein the light emitters are disposed in a radial arrangement.

4. The photobiomodulation system of claim 1, further comprising an imaging device disposed on the distal portion of the lead.

5. The photobiomodulation system of claim 4, wherein the connector of the control module further comprises electrical contacts and the lead comprises conductors coupled to the imaging device and configured for electrically coupling the electrical contacts.

6. The photobiomodulation system of claim 1, wherein the catheter assembly further comprises the catheter pump.

7. A photobiomodulation system, comprising:
   a control module implantable in a patient, the control module comprising
      a housing,
      an electronic subassembly disposed in the housing,
      a connector coupled or coupleable to the housing and defining a lead coupling end, a catheter coupling end, a connector lumen extending from the lead coupling end to the catheter coupling end, and
      at least one light source electrically coupled to the electronic subassembly and configured to produce light in response to signals from the electronic subassembly;
   a lead implantable in the patient, coupled or coupleable to the lead coupling end of the connector of the control module, and having a distal portion spaced apart from the control module, the lead comprising
      a lead body defining a lead lumen that is configured for positioning in fluid communication with the connector lumen of the connector of the control module and a septum disposed in the lead lumen, the lead body further defining at least one opening along the distal portion of the lead and in fluid communication with the lead lumen, a plurality of light emitters arranged along the distal portion of the lead, and a plurality of optical fibers extending along the lead body and coupled to the light emitters and configured to receive light from the at least one light source and deliver the light to the light emitters; and a catheter assembly, comprising a tube coupleable to a catheter pump, and a distal connector attached to an end of the tube and coupled or coupleable to the catheter coupling end of the connector of the control module, the distal connector comprising an assembly lumen extending from the tube and configured for fluid communication with the connector lumen of the connector of the control module and a needle defining a portion of the assembly lumen and configured for penetrating the septum disposed in the lead lumen as the lead and catheter assembly are coupled to the connector of the control module.

8. The photobiomodulation system of claim 1, further comprising a coupling arrangement for coupling the distal connector of the catheter assembly to the catheter coupling end of the connector of the control module.

9. The photobiomodulation system of claim 1, wherein the connector of the control module is detachable from the housing.

10. The photobiomodulation system of claim 1, wherein the connector of the control module further comprises at least one cylindrical lens to receive the light from the at least one light source.

11. The photobiomodulation system of claim 1, wherein the control module further comprises a power source disposed in the housing and coupled to the electronic subassembly.

12. The photobiomodulation system of claim 1, wherein the connector of the control module further comprises one or more seals disposed within or adjacent at least one of the catheter coupling end or the lead coupling end to hinder flow of fluid past the one or more seals.

13. The photobiomodulation system of claim 1, further comprising a programming unit configured to communicate with the electronic subassembly of the control module.

14. The photobiomodulation system of claim 13, further comprising an imaging device disposed on the distal portion of the lead, wherein the programming unit is configured to display images from the imaging device.

15. A method of implanting the lead of the photobiomodulation system of claim 1, the method comprising:

holding the distal portion of the lead using a delivery tool;

inserting the delivery tool into the patient;

guiding the delivery tool and lead to the site of photobiomodulation; and releasing the distal portion of the lead from the delivery tool.

16. The method of claim 15, wherein the delivery tool comprises:

a hand grip arrangement;

a barrel attached to the hand grip arrangement;

a scissor grip for gripping the lead, the scissor grip extending out of the barrel and operatively coupled to the hand grip arrangement, wherein operation of the hand grip arrangement opens and closes the scissor grip; and a vertical steering mechanism extending from the barrel and coupled to the scissor grip to move the scissor grip up and down relative to the barrel without opening or closing the scissor grip.

17. The method of claim 15, wherein the vertical steering mechanism comprises a steering disc, at least one tab extending from the steering disc for rotating the steering disc relative to the barrel, and steering cables attached to, and extending between, the steering disc and scissor grip.

18. The method of claim 17, wherein the lead further comprises an imaging device disposed on the distal portion of the lead, wherein guiding and lead the delivery tool comprises receiving images from the imaging device to guide the delivery tool and lead to the site of photobiomodulation.

19. The method of claim 17, wherein the delivery tool comprises a vertical steering mechanism to move a grip of the delivery tool up or down, wherein guiding the delivery tool and lead comprises using the vertical steering mechanism to facilitate guidance of the delivery tool and lead to the site of photobiomodulation.

20. The photobiomodulation system of claim 7, wherein the catheter assembly further comprises the catheter pump.

* * * * *